United States Patent [19]

Neumaier

[11] 4,016,487
[45] Apr. 5, 1977

[54] ARRANGEMENT OF EDDY CURRENT SCANNING COILS

[75] Inventor: Peter Neumaier, Reutlingen, Germany

[73] Assignee: Institut Dr. Friedrich Forster, Prufgeratebau, Reutlingen, Germany

[22] Filed: Mar. 8, 1976

[21] Appl. No.: 665,009

[30] Foreign Application Priority Data

Mar. 7, 1975 Germany .......................... 2509927

[52] U.S. Cl. .................................. 324/37; 324/40
[51] Int. Cl.² ........................................ G01R 33/12
[58] Field of Search ................... 324/37, 40

[56] References Cited

UNITED STATES PATENTS

| | | | |
|---|---|---|---|
| 2,031,469 | 2/1936 | Drake | 324/37 |
| 2,560,834 | 7/1951 | Whitehead | 324/3 |
| 3,875,502 | 4/1975 | Neumaier | 324/37 |

Primary Examiner—Rudolph V. Rolinec
Assistant Examiner—Michael J. Tokar
Attorney, Agent, or Firm—George J. Netter

[57] ABSTRACT

At least two groups of scanning coils are arranged with respect to the surface of metal parts to be tested at different angles. Means are further provided for oscillating at least one group of scanning coils in a direction generally perpendicular to the normal direction of travel of the scanning coil. Optionally, the exciter windings are rectangular, circular or oval.

8 Claims, 11 Drawing Figures

ARRANGEMENT OF EDDY CURRENT SCANNING COILS

The present invention relates to an eddy current scanning coil arrangement for inspecting the surface of metallic components, in which scanning coils including an exciter winding to generate eddy currents in the part to be inspected and a receiver winding for receiving the signal induced by the eddy current at surface flaws, the axis of the exciter winding being substantially perpendicular to the surface of the part to be inspected and the axis of the receiver winding maintained perpendicular to the axis of the exciter winding.

BACKGROUND

Scanning coils are known which are capable of providing a signal that is a function of the depth of surface flaws when passed over said flaws (such as cracks, etc.) with lengths exceeding the dimensions of the scanning coil, provided the flaw is normal to the axis of the receiver winding in the scanning coil. If, however, such a scanning coil is passed over an extended crack with the axis of the receiver winding coinciding with the direction of the crack, either no signal at all is produced in the event the crack is passed over in a lateral direction, or a signal is produced at the beginning and end of the crack only when the direction of coil travel is parallel to the crack.

In spite of this limitation, scanning coils of the type described are widely used in cases where signals that are strict by a function of the depth are required of long cracks and when these cracks generally run in the same direction (i.e., in the case of rolling stock). The reason is that the design and adjustment of such scanning coils is very simple as compared to differential coils so that large areas can easily be inspected by arranging a number of coils in a line and closely adjacent to each other.

These scanning coils, however, cannot be employed for cracks of any angular orientation in cases where signals corresponding to the crack depth are desired. It was found in the case of the known types of scanning coils described above that the flaw signal is reduced to half its magnitude if the crack angle deviates even 17° from the optimum position. If the deviation from the optimum crack position is 30°, the signal magnitude is only 20% of the signal obtainable for the optimum position.

Frequently the flaw signals are used for crack classification, i.e. for categorizing the flaws in accordance with their seriousness. The measures to be taken then depend upon the category. A prerequisite for this classification, however, is a clear relationship between crack depth and the resulting crack signal. Deviations from the optimum crack position as described above are no longer acceptable.

OBJECTS AND SUMMARY OF THE INVENTION

An object of the present invention is to provide an eddy current scanning coils arrangement which generates signals corresponding to the depth of cracks of any orientation during relative movement of the scanning coil with the surface of the part being inspected. Thus, cracks of any orientation relative to the position of the scanning coil are to be indicated by a signal whose magnitude is substantially independent from the crack direction.

In accordance with the subject invention, at least two groups of scanning coils are arranged with respect to the surface of metal parts to be tested at different angles. Means are further provided for oscillating at least one group of scanning coils in a direction perpendicular to the normal direction of travel of the scanning coil. A great advantage of the scanning coil arrangement in accordance with the present invention lies in its ability to detect all defects of any orientation in just one pass. An additional significant advantage is that the simple construction of the scanning coils used need not be modified.

DESCRIPTION OF PREFERRED EMBODIMENTS

Figure 1:
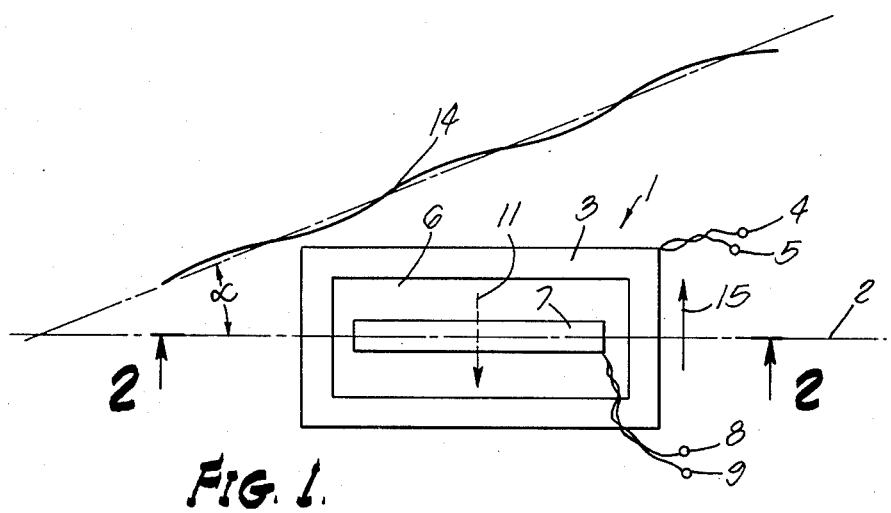
FIG. 1 is an elevational view of a coil.
Figure 2:
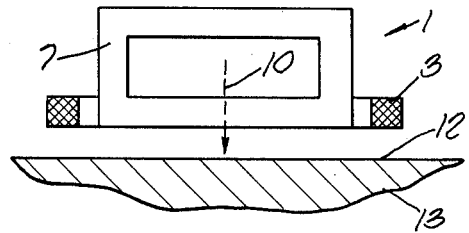
FIG. 2 is a sectional view of the scanning coil taken along the line 2—2 of FIG. 1.

FIGS. 1 and 2 show a scanning coil 1 of known configuration as used in the arrangement described herein, where FIG. 1 is a plan view of the scanning coils and FIG. 2 a sectional view along the axis of symmetry 2. Scanning coil 1 includes a rectangular exciter winding 3 with two end connections 4, 5 and a rectangular receiver winding 7 located in opening 6 of the exciter winding along the axis of symmetry 2, and having winding connections 8 and 9. The two windings 3 and 7 are so arranged that their planes are at right angles or that axis 10 of exciter winding 3 is normal to the axis 11 of receiver winding 7. Scanning coil 1 is also so arranged relative to the surface 12 of a metallic part to be inspected 13 that axis 10 of the exciter winding is perpendicular to surface 12. Crack 14 in surface 12 is oriented at an angle α with axis of symmetry 2. Arrow 15 indicates the direction of travel of scanning coil 1.

Figure 3:
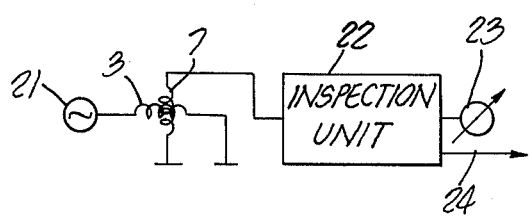
FIG. 3 is a schematic of a circuit for the operation of the scanning coils.

FIG. 3 is a highly simplified electrical circuit required for the operation of scanning coils described in the following. Exciter winding 3 is energized by an a.c. source 21, with the frequency of the current supply depending upon the inspection requirements. Receiver winding 7 is connected to inspection unit 22 which amplifies and rectifies the flaw signals from receiver winding 7 for display on a meter 23, or the signals may be optionally provided at output 24 for further processing.

If scanning coil 1 approaches crack 14 in the direction of arrow 15, the reading on meter 23 increases as soon as the crack comes within the range of exciter winding 3. As the motion continues a first maximum is reached in known manner and then, with crack 14 symmetrical to scanning coil 1, the curve passes through zero, reaches a maximum value of reverse polarity and finally goes back to zero again as scanning coil 1 moves away from crack 14. This signal characteristic is typical for the type of scanning coil under consideration and also for all eddy current scanning coils in simple differential arrangement. For the evaluation of the signals generally, the amount of one of the two maximum values only is of interest. In the following, the maximum value indication only will be referred to.

Figure 4:
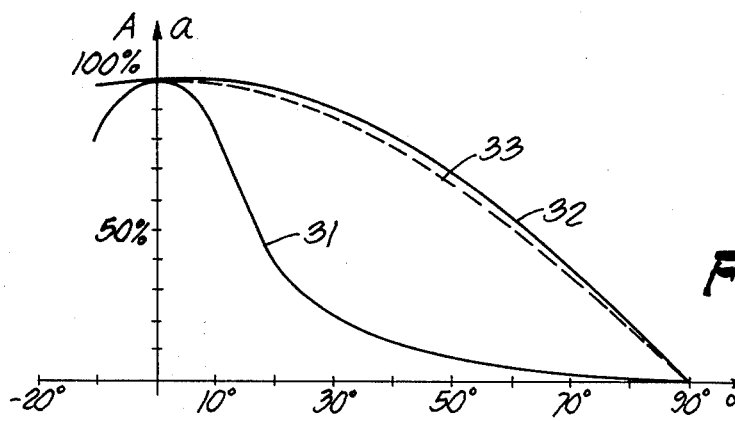
FIGS. 4, 7, and 9 are graphs of the maximum flaw signal amplitudes as a function of the flaw angle.

In graph 31, FIG. 4, the peak values A are plotted as a function of angle $\alpha$ between axis of symmetry 2 of scanning coil 1 and the direction of crack 14. It has been found that for the present type of scanning coil 1, a marked decrease of indicated value A occurs at small angles $\alpha$. As already mentioned above, angle $\alpha = 30°$ causes the value to drop to 20% of the maximum value. As could be expected, for negative angles $\alpha$ curve 31 is similar but inverted so that it is sufficient to show the positive section only.

Figure 5:
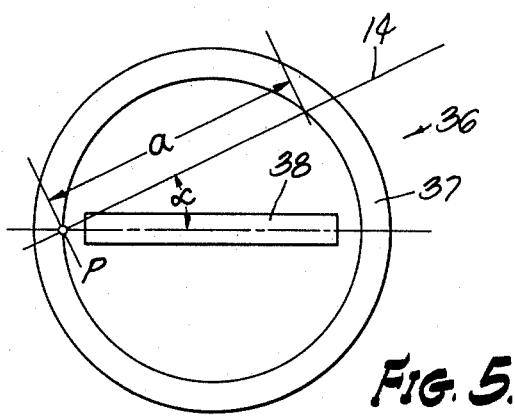
FIG. 5 shows a scanning coil with a circular exciter winding.

FIG. 5 shows scanning coil 36 differing from scanning coil 1 in that exciter winding 37 is of circular shape. Receiver winding 38 is similar to receiver winding 7 and the arrangement of exciter winding 37 and receiver winding 38 relative to each other and relative to the surface of the part to be inspected is maintained, as in the first described version. Curve 32 of FIG. 4 shows the peak value as a function of angle $\alpha$ for scanning coil 36. It can be seen that the characteristic of scanning coil 36 with respect to its dependence upon angle $\alpha$ is much more favourable than in the case of scanning coil 1. For an angle deviation of $\alpha = 45°$, the drop amounts to 25% only. If it is desired to limit the maximum permissible drop to 10%, angle deviations of up to $\pm 30°$ are acceptable.

The dashed curve 33 shows the variations of section $a$ of crack 14, limited by exciter winding 37 as a function of angle $\alpha$, i.e., $a = \cos \alpha$. It is generally assumed that crack 14 passes through the point of intersection P between the axis of symmetry 2 and the inner limitation of exciter winding 37 approximately at the moment where the peak value is indicated. From the great similarity of curves 32 and 33, it may be concluded that a close relationship exists between the size of crack section $a$, limited by the exciter winding at the moment of peak value indication and the amount of peak value A. This, however, would mean that for a wider range within which the indication is independent from angle $\alpha$, an exciter winding of a configuration would be required that initially keeps section $a$ constant on angle $\alpha$ increasing or even causes section $a$ to slightly increase.

Figure 6:
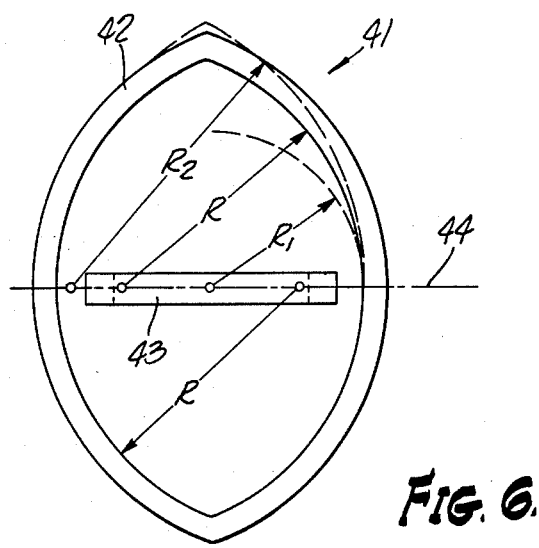
FIG. 6 depicts a scanning coil with an approximately oval field winding.
Figure 8:
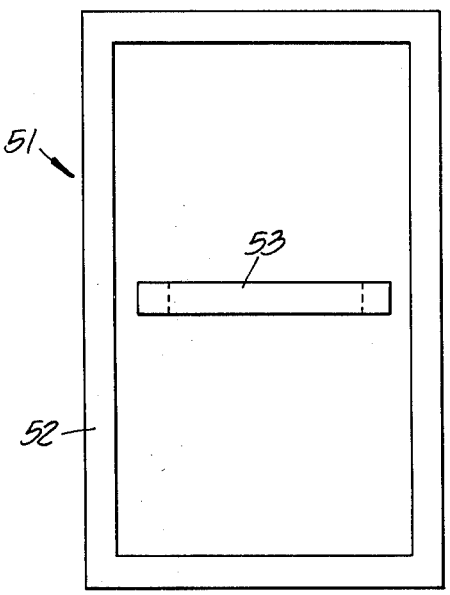
FIG. 8 is a scanning coil with a rectangular exciter winding.
Figure 7:
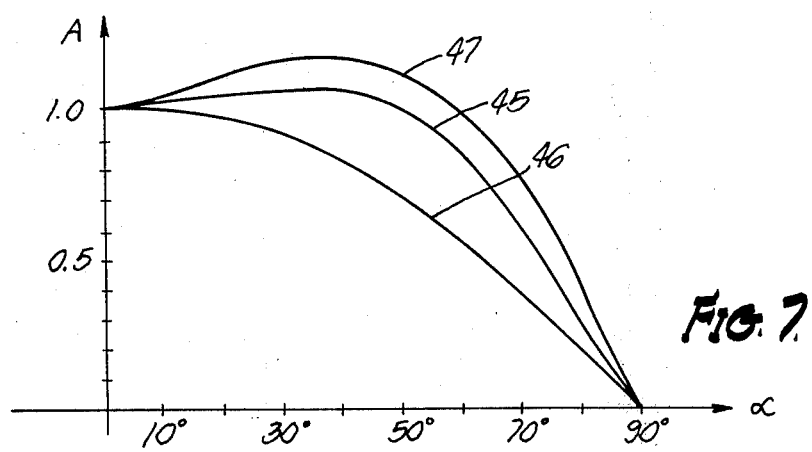
Figure 9:
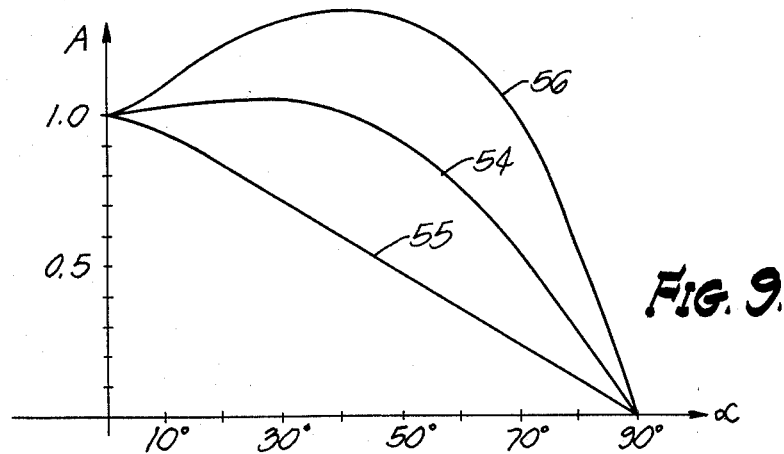

FIGS. 6 and 8 are examples of still further and different exciter winding configurations and FIGS. 7 and 9 show the results obtained, respectively. Scanning coil 41 incorporates exciter winding 42 of approximately oval shape formed by two intersecting circles of radius R and receiver winding 43 of the same design and arrangement as receiver windings 7 or 38. The ratio of the longitudinal to the lateral dimensions of exciter winding 42 is approximately 1.4 to 1. Curve 45, FIG. 7, shows the peak values A resulting as a function of crack angle $\alpha$. It will be found that initially, there is a slight increase of indicated values A. It is only at an angle of $\alpha = 50°$ that the indicated value drops below the value obtained with the crack parallel to the axis of symmetry 44. If deviations of the indicated value up to 15% are allowed, cracks with angle deviations of up to $\pm 60°$ can be covered. For comparison, curve 46 of a scanning coil with a circular exciter winding of radius $R_1$, i.e., with ratio 1 between longitudinal and lateral dimensions, is again shown below curve 45. Curve 47, however, represents the characteristic of a scanning coil with an exciter winding of radius $R_2$, with the ratio between the longitudinal and lateral dimensions of the exciter winding being approximately 1.6 to 1. Here with increasing $\alpha$ a marked overindication of the peak values becomes apparent. This effect becomes more significant with an increase of the ratio between longitudinal and lateral dimensions. On the other hand, scanning coils are relatively insensitive to variations of the crack direction when selecting an exciter winding of purely elliptical form, while retaining the above ratio. Moreover, tests have shown that the length and height of receiver winding 43 has no significant influence upon the curves in FIG. 7.

FIGS. 8 and 9 demonstrate that with rectangular exciter windings an improved characteristic of the scanning coils with respect to crack angle deviations can be obtained by selecting a favourable ratio between the longitudinal and lateral dimensions. The constant range, however, that can be obtained is no longer as large as it was for the case of an oval or approximately oval exciter winding. Scanning coil 51 again incorporates an exciter winding 52 and receiver winding 53 related to each other as already described. Curve 54 shows the characteristic of peak value A when employing scanning coil 51 as shown whose exciter winding has a ratio of 1.6 to 1. Thus, for an acceptable deviation of indication A of 15%, a useful range of $\pm 53°$ is still obtainable. Curve 55 represents a scanning coil with a rectangular exciter winding of ratio of 1 to 1, i.e. of square shape. In this case, angle $\alpha$ is accompanied by an almost linear decrease of peak value A. Curve 56 represents a scanning coil whose rectangular exciter winding has the ratio of 1.9 to 1, and in which case, on increasing values of $\alpha$ a marked overindication of the maximum value occurs.

Generally, it can be said that by selecting a favourable ratio between the longitudinal and lateral dimensions of the exciter winding, scanning coils can be provided where over a wide range, the peak value indications when passing over a crack are practically independent from the crack angle position.

Figure 10:
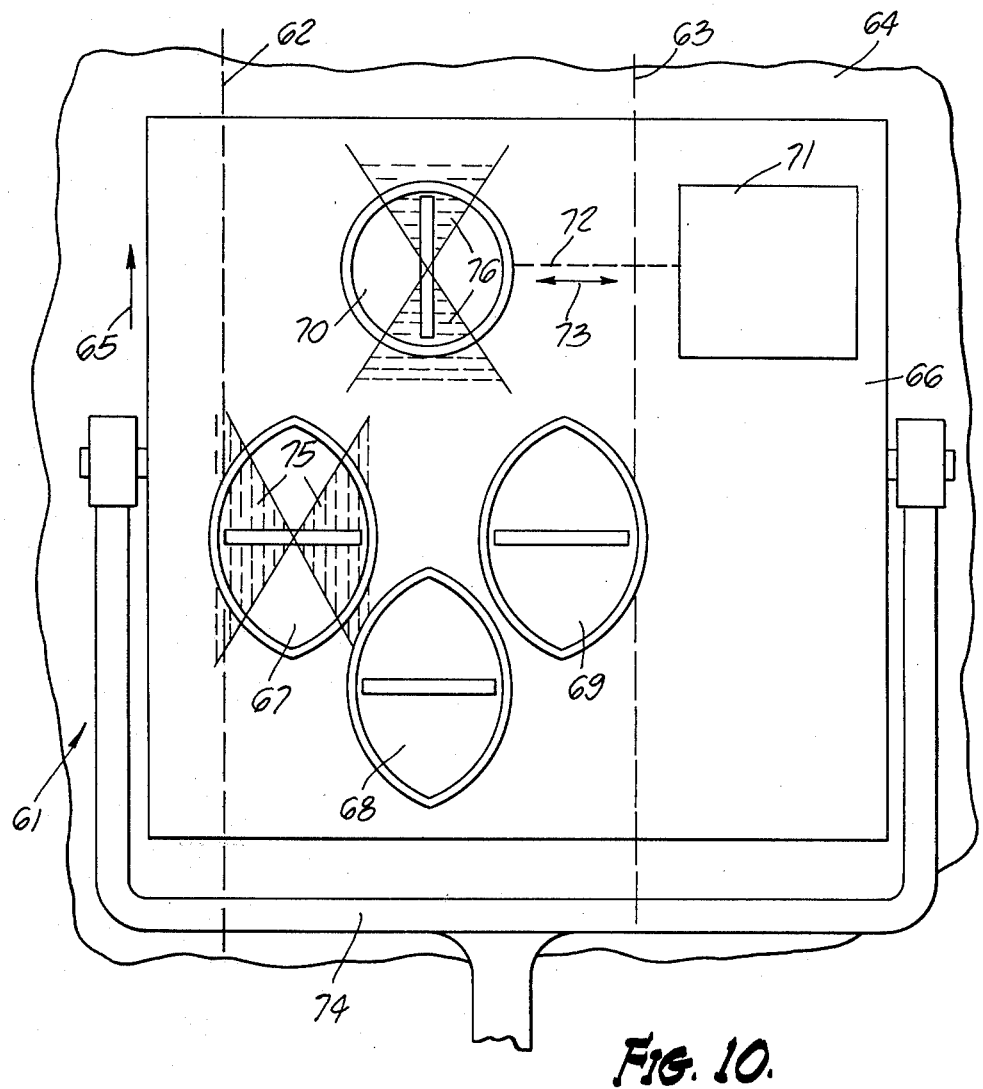
FIG. 10 shows one form of scanning coil arrangement.

FIG. 10 shows a scanning coil arrangement 61 capable of indicating all surface flaws within the surface area of the part to be inspected 64, identified by dashed lines 62, 63, independent of the crack direction, with the indication corresponding to the crack depth, while scanning coil arrangement 61 passes over the part surface in the direction of arrow 65. The part 65 to be inspected might be a slab and during the inspection of the surface of the slab, a number of scanning coil arrangements 61 may be passed simultaneously over the slab surface in order to cover a maximum surface area in one pass.

Scanning coil arrangement 61 consists substantially of a scanning coil carrier 66, three scanning coils 67, 68, 69 fixed thereon, one scanning coil 70, movable in a direction perpendicular to arrow 65, vibration generator 71 subjecting scanning coil 70 to an oscillating motion in the direction of arrow 73 via coupling means 72 between limits 62 and 63 and fork-type support 74 for the carrier 66. The three scanning coils 67, 68, 69 are of type 41 and so arranged that they cover the whole width of the surface of the part 64 to be inspected between limits 62 and 63, with the individual coil ranges overlapping. Preferably, the scanning coils are arranged offset relative to each other along the direction of motion. The hatched areas 75 of scanning coil 67 indicate within which angle range cracks are indicated with full sensitivity, i.e. within −60°<α<+60°, with 15% maximum deviation of the indicated value. Scanning coil 70 is of the same type as coil 36 and is passed over the cracks or defects by vibration generator 71 in oscillating motion. The hatched areas 76 indicate within which angle range cracks or defects are indicated with full sensitivity. In this case, the range within which the deviation does not exceed 15% is −35°<α<+35°. The ranges 75 and 76 are complementary so that they cover at least a full circle, i.e. the depth of defects of any angular position is fully indicated.

Figure 11:
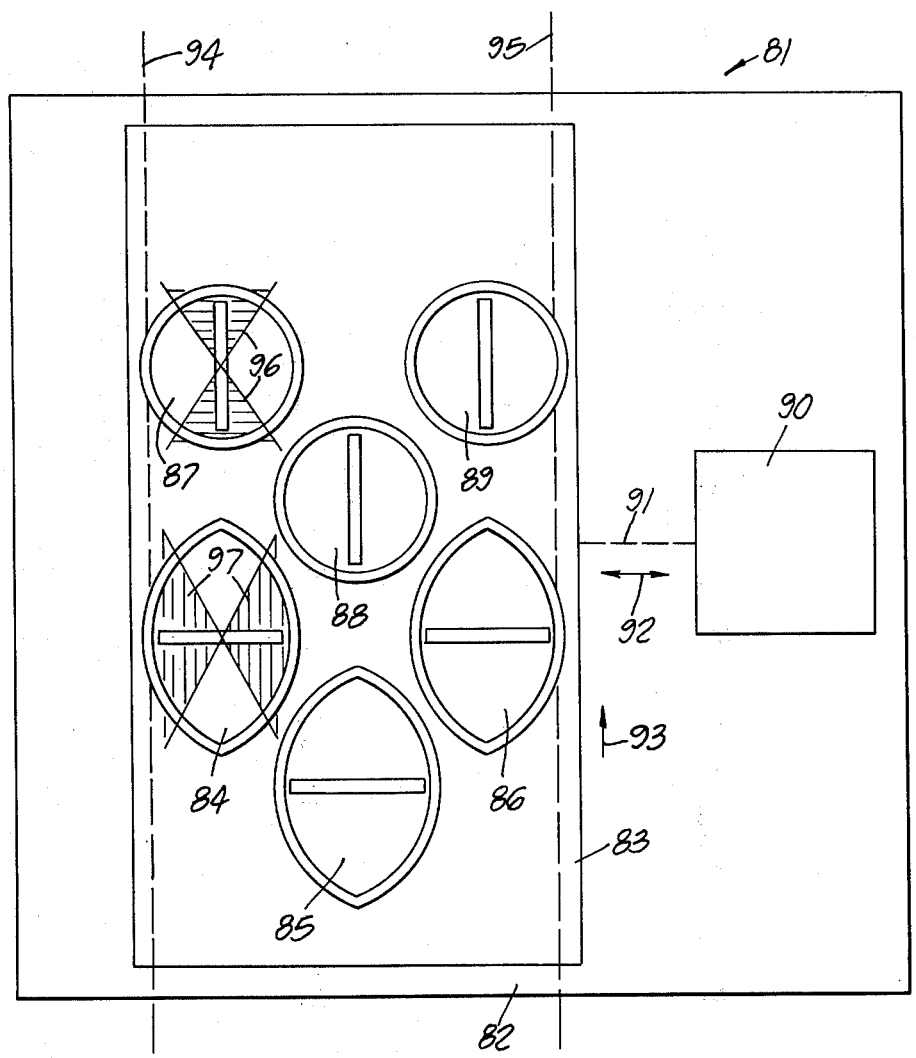
FIG. 11 shows an alternate form of scanning coil arrangement.

In scanning coil arrangements of the above described type, the oscillating and fixed scanning coils must be arranged at a distance sufficient to ensure trouble-free operation. Otherwise, the locally changing eddy current fields generated by the oscillating exciter windings would induce pseudo signals in the receiver winding of the fixed scanning coils, which are very difficult to compensate. This problem can be solved by a scanning coil arrangement 81 as shown in FIG. 11, comprising a baseplate 82, scanning coil carrier 83 with fixed scanning coils 84, 85, 86 or 87, 88, 89, and a vibration generator 90, subjecting scanning coil carrier 83 to an oscillating motion in the direction of arrow 92 via coupling means 91, while the scanning coil arrangement 81 is moving linearly in the direction of arrow 93. For scanning the area between limits 94, 95 in the present case, a vibration amplitude is sufficient which roughly corresponds to the radius of the exciter winding of scanning coils 87, 88, 89. Scanning coils 84, 85, 86 are of the same type as scanning coil 41; scanning coils 87, 88, 89, however, are of the same type as scanning coil 36. Ranges 96 and 97 of constant sensitivity of scanning coils 84, 85, 86 or 87, 88, 89, respectively, are again complementary as described above for scanning coil arrangement 61, so that ranges 96 and 97 cover at least 360°, i.e., defects of any angular position are fully indicated in accordance with their depth.

Scanning coil arrangements may of course also include scanning coils of identical characteristic, e.g., type 41 coils only. The reason why in the above described examples for one group scanning coils with circular exciter windings were used, is their shorter space-saving length providing an angle range that is sufficient for the case considered. It is of great importance that the individual groups have different crack angle ranges adding up to 360°, e.g., the ranges 75 and 76 or 96 and 97. Although in most cases, two groups of scanning coils are sufficient, more than two groups might also be employed. Moreover, the axes of the scanning coil receiver winding do not necessarily have to point in the direction of the scanning coil motion. It might be of advantage to position the axes of the receiver windings of one group of scanning coils at an angle of +45° and the other group at an angle of −45° relative to the direction of motion. In each case, however, a motion perpendicular to the direction of motion must be superimposed to at least one of the scanning coil groups so that defects whose direction coincides with the direction of motion, are fully indicated.

I claim:

1. An arrangement of eddy current scanning coils for determining the presence of surface and near-surface defects in a metal part moving relatively thereto, each scanning coil including an exciter winding for producing eddy currents in the metal part and a receiver winding for receiving signals produced by defects, the exciter winding axis being substantially normal to the part surface being scanned and the receiver winding axis being perpendicular to the exciter winding axis, the improvement comprising:
   the scanning coils being arranged in at least two groups, with the scanning coils of the groups being oriented to be effective for different angular ranges of defects; and
   means provided for oscillating at least one scanning coil normally to the direction of relative movement between the scanning coils and metal part.

2. An arrangement of eddy current scanning coils as in claim 1, in which the receiver windings of one group have their axes aligned with the direction of relative movement, and the scanning coils of the other group are oscillated substantially perpendicularly to the direction of relative movement.

3. An arrangement as in claim 1, in which said groups of scanning coils are mounted on a common carrier, the receiver winding axes of one group of coils being aligned with the direction of relative movement, and the axes of the scanning coils of the other group being perpendicular to the direction of relative movement; and there are further provided means for oscillating the carrier substantially perpendicularly to the direction of relative motion.

4. An arrangement as in claim 1, in which the axes of the receiver windings of one group are disposed at +45° to the direction of relative movement and the axes of the receiver windings of the other group at −45° thereto.

5. An arrangement as in claim 1, in which the exciter winding of at least one group of scanning coils is of circular geometry.

6. An arrangement as in claim 1, in which the exciter windings of at least one group of scanning coils are generally oval in shape.

7. An arrangement as in claim 6, in which the length to width ratio of the oval exciter windings is substantially 1.4 to 1.

8. An arrangement as in claim 1, in which the exciter windings of at least one group of scanning coils are rectangular with the ratio of length to width being substantially 1.6 to 1.

* * * * *